United States Patent
Piriz Niblon

(10) Patent No.: US 8,141,554 B2
(45) Date of Patent: Mar. 27, 2012

(54) ORAL PROPHYLACTIC DEVICE

(76) Inventor: Pino Octavio Piriz Niblon, Maldonado (UY)

( * ) Notice: Subject to any disclaimer, the term of this patent is extended or adjusted under 35 U.S.C. 154(b) by 580 days.

(21) Appl. No.: 12/119,585

(22) Filed: May 13, 2008

(65) Prior Publication Data

US 2009/0078269 A1   Mar. 26, 2009

(51) Int. Cl.
*A61F 6/06* (2006.01)
*A61F 6/02* (2006.01)
*A61F 6/04* (2006.01)

(52) U.S. Cl. ........ 128/859; 128/831; 128/834; 128/842; 128/844; 128/917; 128/918

(58) Field of Classification Search ............ 128/831, 128/834, 842, 844, 917, 918, 859; 600/38–41
See application file for complete search history.

(56) References Cited

U.S. PATENT DOCUMENTS

| | | | | | |
|---|---|---|---|---|---|
| 4,949,731 | A | * | 8/1990 | Harding | 128/842 |
| 5,069,228 | A | * | 12/1991 | Sorkin | 128/844 |
| 5,083,414 | A | * | 1/1992 | Wu | 53/429 |
| 5,156,165 | A | * | 10/1992 | Wu | 128/844 |
| 5,390,681 | A | * | 2/1995 | Daley | 128/842 |
| 5,515,862 | A | * | 5/1996 | Artsi et al. | 128/830 |
| 5,857,466 | A | * | 1/1999 | Sadlo | 128/844 |
| 5,992,415 | A | * | 11/1999 | Alla et al. | 128/830 |
| 7,726,316 | B1 | * | 6/2010 | Pope | 128/830 |
| 2002/0038658 | A1 | * | 4/2002 | Austin et al. | 128/830 |
| 2006/0081264 | A1 | * | 4/2006 | Vera | 128/884 |

* cited by examiner

*Primary Examiner* — Patricia Bianco
*Assistant Examiner* — Brandon Jackson
(74) *Attorney, Agent, or Firm* — Zarley Law Firm, P.L.C.

(57) ABSTRACT

It is hereby described an oral prophylactic device constructed of vulcanized natural latex or similar material, having a reinforced edge, a crown-shaped middle portion slightly thinner and a central portion representing a protuberance similar to a nipple (though bigger in size) which is absolutely flexible due to its lower thickness. It allows the practice of oral-vaginal or anal sexual intercourse without any risk of contagion of venereal diseases or AIDS and it also eliminates foul smells.

2 Claims, 2 Drawing Sheets

ORAL PROPHYLACTIC DEVICE

FIELD OF THE INVENTION

The present invention relates to an "oral prophylactic device", i.e. an oral protector against possible sexually transmitted diseases. Said device forms part of the field related to the industry of sexual prophylaxis.

BACKGROUND OF THE INVENTION

It has been demonstrated that lately the so-called oral sex has diminished during sexual intercourse (due to the fear of contagion, not only of AIDS, but of venereal diseases such as syphilis or chancroid, condyloma, gonorrhea, etc.), resulting in a decrease of sexual pleasure which should naturally exist during sexual intercourse, as the necessary steps for greater pleasure prior to intercourse are skipped. When there is a lack of oral sex in a couple's relationship, it is looked for outside the relationship and individuals engage in sexual intercourse with occasional partners or hire the services of prostitutes or taxi boys, thus increasing the risk of contagion of venereal diseases or HIV, which may eventually turn into AIDS. This is also applicable to homosexual couples (gays or lesbians), where fear is greater by virtue of the higher number of occasional contacts among them.

The designed oral protector allows the couple to fully enjoy sexual intercourse, avoiding direct anal, vaginal and oral—mouth and tongue—contact; it also masks foul smells; likewise, it protects individuals who suffer from pyorrhea and other dental infections who cannot engage in oral sex for these reasons.

The designed oral protector can be indiscriminately used during any type of oral-anal or vaginal intercourse, for which reason it is useful in both hetero and homosexual (gays and lesbians) relationships.

SUMMARY

An oral protector constructed of vulcanized natural latex or similar material having an outer edge reinforced or thicker on a middle portion of lower thickness having at the center a nipple-shaped protuberance that is thinner and more flexible.

DETAILED DESCRIPTION OF THE PREFERRED EMBODIMENT

The conceived oral protector is constructed of natural latex or vulcanized latex sheets or sheets of a similar material, is circular or polygonal-shaped and the dimensions thereof are suitable for the intended application. It is composed of three portions: a reinforced peripheral edge (1) slightly thicker, a crown-shaped middle portion (2) and a central portion (3) representing a protuberance similar to a nipple but bigger in size and significantly thinner. As such it provides the tongue, which is the organ making contact with said protuberance or surrounding area, with a higher flexibility, all which will provide greater pleasure to those engaged in the intercourse. The edge of this protector is reinforced to prevent the breakage thereof while handling it.

Functioning or Use

The utilization of this oral protector is extremely simple as it only requires the application of a cream or gel on the protector, which will then be placed on the corresponding area (anus or vagina). The cream or gel will act as an adhesive and the user will be able to use his/her hands freely to caress his/her partner without limitations. Once the protector is placed with the cream or gel over the user's mouth, he/she will put his/her tongue in the central portion or protuberance similar to a nipple (though bigger in size) and will start moving it to give pleasure to his/her partner. The user will be sheltered from contamination and foul smells and will be able to use a finger as a substitute for the tongue, if he/she so wishes it.

BRIEF DESCRIPTION OF THE DRAWINGS

By way of example, without implying a limitation on the scope of protection, there are attached drawings with references to facilitate the understanding of the above description.

Figure 1:
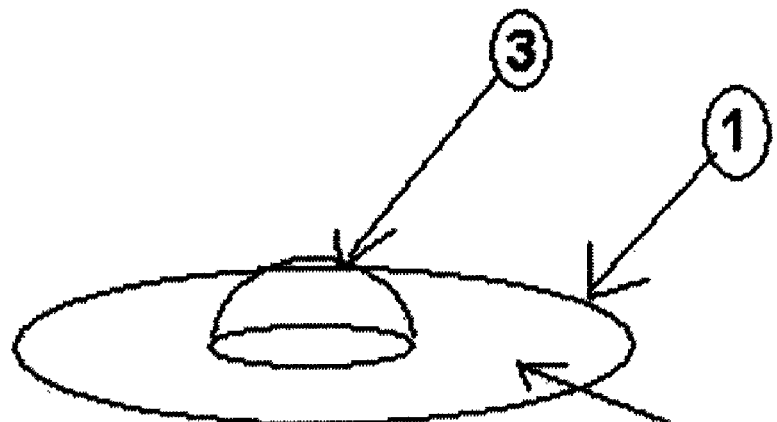
FIG. 1—A side view of the oral protector, showing at the top a protuberance (3), simulating a nipple (though bigger in size) constructed of latex or similar material, of lower thickness, inside of which the user puts his/her tongue to perform oral sex on his/her partner.
Figure 2:
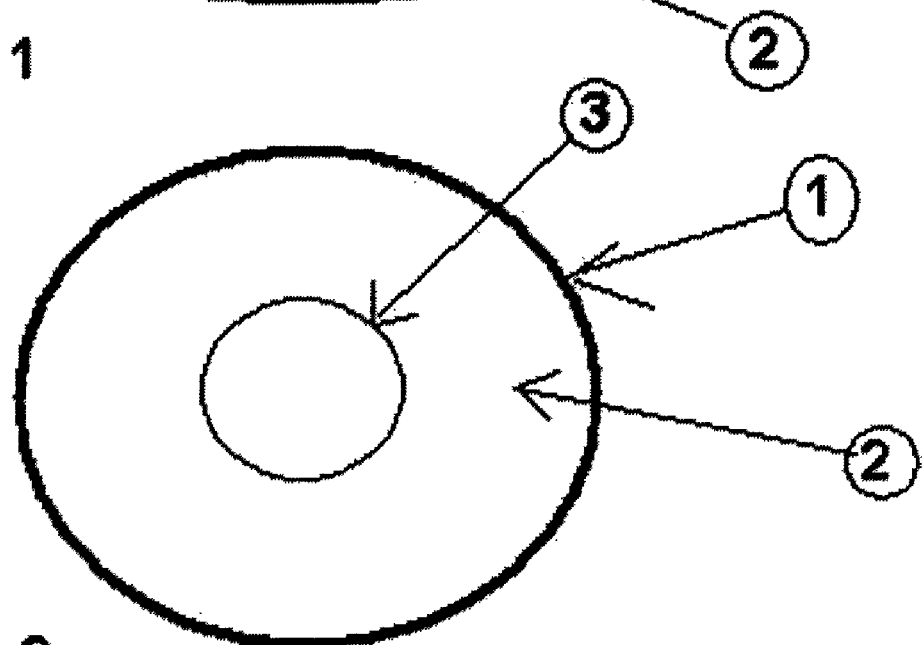
FIG. 2—A horizontal view of the oral protector, showing a reinforced outer edge (1) and a middle portion (2) thereof which is bigger in size and lies against a gel or cream, and a central part which is thinner and thus more flexible, where the user puts his/her tongue or finger to give pleasure to his/her partner.
Figure 3:
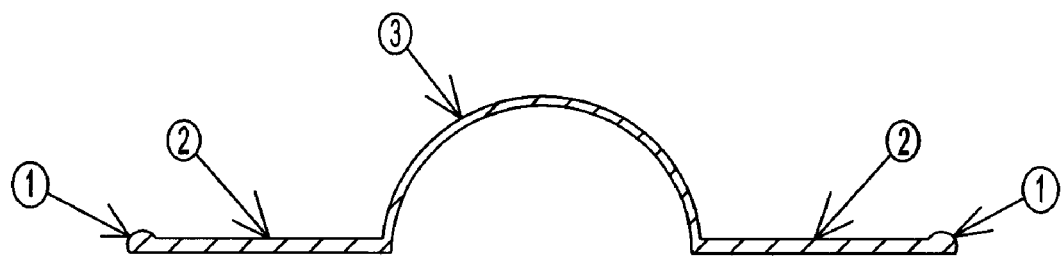
FIG. 3—A side cross sectional view of the oral protector of the present invention.

Having described the nature of the present invention and the way to put it into practice, it is hereby claimed the exclusive ownership of the invention according to the following detail:

The invention claimed is:

1. An oral protector comprising:
   an outer reinforced peripheral edge made of flexible material having a first thickness,
   a middle portion extending from the outer edge which is larger in size and made of the flexible material having a second, lower thickness than the first thickness of the outer peripheral edge; and
   a flexible nipple-shaped protuberance made of the flexible material extending from the middle portion and having a third thickness that is less than the thickness of the middle portion such that the flexible nipple-shaped protuberance is provided with higher flexibility.

2. The oral protector of claim 1 wherein an adhesive substance is spread over the middle portion of the protector.

* * * * *

UNITED STATES PATENT AND TRADEMARK OFFICE
Certificate

Patent No. 8,141,554 B2                                                                      Patented: March 27, 2012

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Nelly Maria Gonzalez Olivera, Montevideo (UY).

Signed and Sealed this Fifth Day of February 2013.

*JUSTINE R. YU*
*Supervisory Patent Examiner*
Art Unit 3771
Technology Center 3700